(12) United States Patent
Baumgartner

(10) Patent No.: US 6,582,924 B1
(45) Date of Patent: Jun. 24, 2003

(54) HAIR ANALYSIS METHOD

(75) Inventor: Werner A. Baumgartner, Malibu, CA (US)

(73) Assignee: Psychemedics Corporation, Cambridge, MA (US)

( * ) Notice: Subject to any disclaimer, the term of this patent is extended or adjusted under 35 U.S.C. 154(b) by 0 days.

(21) Appl. No.: 08/393,232

(22) Filed: Feb. 23, 1995

Related U.S. Application Data

(63) Continuation of application No. 08/170,638, filed on Dec. 21, 1993, now abandoned, which is a continuation of application No. 07/590,953, filed on Oct. 1, 1990, now abandoned, which is a continuation-in-part of application No. 07/285,123, filed on Dec. 16, 1988, now Pat. No. 5,324,624, which is a continuation-in-part of application No. 07/215,591, filed on Jul. 6, 1988, now abandoned, which is a continuation-in-part of application No. 08/138,515, filed on Dec. 28, 1987, now abandoned.

(51) Int. Cl.$^7$ .................. G01N 33/53; G01N 33/563; C12Q 1/37
(52) U.S. Cl. .................. 435/7.1; 435/23; 435/24; 435/961; 435/972; 436/512; 436/518; 436/177; 436/175
(58) Field of Search .................. 435/7.1, 23, 24, 435/265, 267, 961, 962; 436/175, 177, 518, 816, 825, 901, 512

(56) References Cited

U.S. PATENT DOCUMENTS

| 3,873,682 A | 3/1975 | Ogawa ................ 436/518 X |
| 4,963,658 A | * 10/1990 | Kung et al. ................ 435/6 X |
| 5,324,642 A | 6/1994 | Baumgartner ............ 435/7.1 |

OTHER PUBLICATIONS

Offidani et al., *Forensic Sciences International*, vol. 41, No. 1/2, pp. 35–39, (1989).*
Geisen et al., *Hair Research*, [Proc. Int. Congr.], 1$^{st}$, Meeting Date 1979, pp. 138–139, (1981).*
Baumgartner et al., *Clin. Nucl Med.*, [Soc. Nucl. Med., 10$^{th}$ Ann West. Reg. Mtg.] Meeting Date Sep. 1985. vol. 10, p 4.*
Valente et al. *Clin. Chem.* vol. 27 No. 11, pp. 1952–1953, (1981).*
Gainer, et al. *Virology*, vol. 45, pp. 91–100, (1971).*
Costa et al, *Biochem. Biophys. Res. Comm.*, vol. 78, No. 2, (1977), pp. 596–603.*
Kimmel et al., "The Properties of Papain," in *Advances in Enzymology*, vol. 19, F.F. Nord, Ed., (1957), pp. 267–334.*
Zahler et al., *J. Biol. Chem.*, vol. 243, No. 4, pp. 716–719, 1968.*
Millipore Catalog, 1990, pp. 198–199.*
*Clelano's Reagent*, Cal Biochem Doc. No. 4926–285, pp. 11, 22, and 24–25.*
A.W. Holmes, "Degradation of Human Hair by Papain", *Textile Research Journal*, Aug. 1964, pp. 706–712.
Biaglow et al., "Facters Influencing the Oxidation of Cysteamine and Other Thiols: Implications for Hyperthermic Sensitization and Radiatio Protection", *Radiation Research*, vol. 100, pp. 298–312 (1984).
H. P. Misra, "Generation of Superoxide Free Radical during the Autoxidation of Thiols", *The Journal of Biological Chemistry*, vol. 249, No. 7, pp. 2151–2155 (1974).
P.C. Jocelyn, *Biochemistry of the SH Group*, Academic Press, New York, pp. 94–115 (1974).

\* cited by examiner

*Primary Examiner*—Long V. Le
*Assistant Examiner*—Changhwa Jacob Cheu
(74) *Attorney, Agent, or Firm*—Dewey Ballantine LLP

(57) ABSTRACT

A method for the direct analysis of analyte in keratinized structures, e.g., hair, fingernails and toenails, which comprises preparing a mixture containing a low redox potential compound such as dithiothreitol or dithioerythritol, an enzyme suitable for the degradation of the keratin structure and a sample of the keratin structure; permitting the enzyme to at least substantially degrade the sample of keratin structure, filtering the digest solution to remove substances which may interfere with ligand based analytical methods and subjecting the filtered digest solution to analysis to determine the identity and amount of analyte in the keratin substance sample. To accelerate the method, cupric sulfate may be added to the mixture after degradation of the keratin sample. The enzyme may be a peptidase, endopeptidase or proteinase, with papain, chymopapain, and proteinase K being preferred for use in the invention. The filter preferably is of the centrifugal type, characterized by a highly inert and low binding, regeneraged de-acetylated cellulose membrane and capable of removing proteins and peptides having molecular weights in the preferred range of 10,000 to 30,000 or greater.

11 Claims, No Drawings

HAIR ANALYSIS METHOD

CROSS REFERENCE TO RELATED APPLICATIONS

This application is a continuation of U.S. application Ser. No. 08/170,638 filed Dec. 21, 1993, now abandoned, which is a continuation of U.S. application Ser. No. 07/590,953 filed Oct. 1, 1990, now abandoned, which in turn is a continuation-in-part of U.S. application Ser. No. 07/285,123 filed Dec. 16, 1988, now U.S. Pat. No. 5,324,624, which in turn is a continuation-in-part of U.S. application Ser. No. 07/215,591 filed Jul. 6, 1988, now abandoned which in turn is a continuation-in-part of U.S. application Ser. No. 08/138, 515, filed Dec. 28, 1987, now abandoned.

FIELD OF THE INVENTION

This invention relates to an improved analytical method which effectuates the relatively rapid solubilization of hair and direct analysis of organic analytes, e.g., drugs of abuse, present in hair and other keratinized structures, e.g., fingernails and toenails, without effecting the structure of the analyte or being detrimental to biological analyte probes, e.g., antibody, RNA/DNA and bio-receptor probes. The analyte can be analyzed by adding the analyte probe directly to the solubilized keratin structure containing the analyte to determine the identity of the analyte as well as the extent and duration of its consumption by a subject.

BACKGROUND OF THE INVENTION

In the past, hair analysis techniques for the detection of trace metals were developed that purported to provide information on an individual's nutritional status. One objection to the use of these techniques is the difficulty of distinguishing between trace metals deposited in hair from the bloodstream and metals which have become embedded in hair through external contact with, for example, water and cosmetic agents. Consequently, these techniques are not considered useful by the medical community for diagnosing nutritional problems, and therefore have not been considered sufficiently accurate to determine the level of a particular trace metal consumed by a subject.

The problems with previous hair analysis techniques have caused reliance on urine and blood analysis techniques for the detection of ingested chemicals, e.g., drugs-of-abuse, medications and toxic chemicals, in a subject. However, these techniques are also known to be disadvantageous in that the duration and intensity of use or exposure cannot be ascertained. Urine and blood analysis, at best, can provide short term information concerning ingested drugs or chemicals such as drugs-of-abuse. In addition, there are also problems with the interpretation of such results. For example, the detection of a low level of ingested chemical in the urine could mean that a subject ingested a small amount of the drug or chemical very recently or a larger amount several days earlier. Thus, chronic drug use cannot be determined with these methods without repeated testing.

In response to the problems of establishing a reliable and accurate method that would measure both the duration and intensity of use of drugs-of-abuse, medications, toxic chemicals, etc., work performed by Dr. Werner A. Baumgartner, as reported in "Radioimmunoassay of Hair for Determining Opiate Abuse Histories", J. Nucl Med 20:749–752 (1979), determined that long-term histories of exposure to drugs-of-abuse can be obtained through the analysis of mammalian body hair, since these substances are "trapped" within individual hair fibers during their synthesis. In this respect, hair was shown to act like a tape recorder, i.e., past exposure histories can be evaluated through sectional analysis of hair samples. It was found that heroin, once in the bloodstream, will find its way into hair as it is synthesized.

Thus, it was discovered in this study and confirmed by subsequent studies that a variety of chemicals, such as drugs-of-abuse, medications, toxic chemicals, etc., hereinafter collectively referred to as "analyte", are trapped by hair during its synthesis and that these substances are "locked up" in hair for essentially the duration of the hair. This was found to be true for head and body hair as well as for other keratinized structures such as fingernails. Suzuki et al., Forensic Sci. International, 24:9–16, 1984. These entrapped substances cannot be washed out of hair, and are released only upon complete destruction of the hair fiber.

Prior art methods of extracting an analyte from hair included subjecting the hair to hot methanol solutions (Baumgartner et al., J. Nucl Med 20, 748, 1979) and by overnight incubation of hair in an alkaline or acid medium. D. Valente, et al., Clinical Chemistry, 1952, Vol. 27, No. 11, 1981. Prior methods also include the use of a mortar and pestle to release the entrapped analyte in conjunction with a solvent.

However, solvent extraction procedures suffer from several problems in accurately determining the presence and amount of an ingested analyte. One of these problems is that the solvent extraction methods frequently remove only a small unknown and variable fraction of the total analyte present in the hair sample. Such methods also tend to be time consuming, and generally involve elevated temperatures which may damage the analyte. Another disadvantage is that different analytes require different solvents for extraction. For example, a hair sample containing morphine, phenylcyclindine ("PCP"), cocaine and marijuana has to be extracted sequentially with several different solvents, which is a very time consuming procedure, particularly since the solvents have to be evaporated before analysis can proceed.

Other methods and studies pertaining to the degradation of hair and hair analysis include:

O. Suzuki, et. al., in a publication by Elsevier Scientific Publishers Ireland Ltd., discloses a method for detecting methamphetamine and amphetamine in nail clippings or hair in which the substance was first washed in a mixture of methanol and water and dissolved in sodium hydroxide, followed by analysis of the extracted drug.

A. W. Holmes, in Textile Research Journal, 706–712, August 1964, discloses the degradation of human hair by papain using sodium sulfite as enzyme activator.

Annette M. Baumgartner, et al., in the Journal of Nuclear Medicine, 20:748–752, 1979, discloses the extraction of morphine and heroin from hair by pulverizing hair with a mortar and pestle followed by treatment with methanol.

D. Valente, et al., in Clinical Chemistry, Vol. 27, No. 11, 1981, discloses Dr. Baumgartner's technique of subjecting hair to a treatment of hot methanol to effectuate extraction of drugs of abuse as well as the author's technique of extracting morphine in an acid or alkaline medium.

A. M. Baumgartner, et al., in Journal of Forensic Sciences, p. 576–81, July 1981, discloses the extraction of PCP with mortar and pestle followed by treatment with methanol. The extracted PCP was then analyzed with RIA.

Smith et al., in Journal of Forensic Sciences, Vol. 26, No. 3, July 1981, pp. 582–586, disclose the testing of hair for the presence of phenobarbitol, in which a single head hair was washed, dried, cut in 2 mm lengths and added to 0.2 ml 0.1% SDS/saline solution, and a sample assayed by radioimmunoassay.

W. A. Baumgartner, Black, et al., in J. Nucl Med 23: 790–892, 1982, discloses the extraction of cocaine from hair samples by refluxing the hair samples in ethanol followed by RIA analysis.

Ishiyama, et al., in Journal of Forensic Sciences, Vol. 28, No. 2, April 1983, pp. 380–385, disclose a method whereby hair from methamphetamine addicts was dissolved using 1.5 N hydrochloric acid at a pH between 1 and 2, followed by analysis using a gas chromatograph and mass spectrometry.

K. Puschel, et al., in Forensic Science International, 21 (1983) 181–186, discloses the dissolving of hair samples by exposure to sodium hydroxide and heat followed by analysis for the presence of morphine by RIA.

O. Suzuki, et al., in Journal of Forensic Sciences, Vol. 29, No. 2, April 1984, pp. 611–617, discloses the detection of methamphetamine and amphetamine in a single human hair by gas chromatography and chemical ionization mass spectrometry. The hair sample was first dissolved in a sodium hydroxide solution to which was added N-methylbenzylamine.

N. J. Haley et al., in Clin. Chem. 31/10, 1598–1600 (1985), discloses the analysis of hair for nicotine and cotinine, in which washed hair samples were dissolved in a buffer solution containing gelatin, sodium chloride, Tris and EDTA, and adjusted to pH 7.4. Samples were then analyzed by radioimmunoassay.

Sramek, Baumgartner, et al., in A. M. J. Psychiatry 142:8, August 1985, discloses the analysis of hair samples of psychiatric patients with methanol extraction and radioimmunoassay.

Baumgartner, et al., in Clinical Nuclear Medicine, vol. 10, September 1985, discloses the benefits of extracting entrapped drugs of abuse from hair followed by RIA analysis.

Gill, et al., in Nature, Vol. 318, p. 577 (1985) discloses the use of an SDS/proteinase k/dithiothreital mixture to extract DNA from whole blood, whole semen, vaginal fluid, hair roots, bloodstains and semen stains. The article states that "no DNA could be isolated from hair shafts".

Smith et al., in J. Forensic Sci. 1986, 31(4), 1269–73, discloses the detection of cocaine in perspiration, menstrual blood stains and hair using RIA.

M. Margio, et al., in "Determination of Morphine and Other Opioids in the Hair of Heroin Addicts by HPLC and MS/MS" at the International Conference, University of Verona, Jun. 25–26, 1986, discloses various methods to assay morphine from hair samples.

M. Marigo, et al., in the Journal of Analytical Toxicology, Vol. 10, July/August 1986, discloses a method for the quantitative determination of morphine contained in the hair of heroin addicts, by means of heat-acid hydrolysis, pre-column dansyl derivatization, straight phase liquid chromatography and fluorescence detection.

Smith, et al., in Journal of Forensic Sciences, Vol. 31, No. 4, October 1986, pp. 1269–1273, disclose a method for the analysis of hair for the presence of drugs whereby hair samples were first washed, cut into small segments, mechanically pulverized for six minutes, refluxed in ethanol and the samples analyzed using radioimmunoassay.

M. Michalodinitrakis, Med.Sci.Law (1987), Vol. 27, No. 1, discloses the detection of cocaine in rats from the analysis of hair samples, which were dissolved upon exposure to 1.5 N HCL, which brought the pH value to 1–2, following incubation with 0.01 N HCl at 37° C. for one hour.

Pelli, et al., in Biomedical and Environmental Mass Spectrometry, Vol. 14, 63–68 (1987) discloses a procedure for the identification of morphine in the hair of heroin addicts in which hair is treated with diethylether and hydrochloric acid followed by dissolution of the dried extract in methanol.

Higuchi et al., in Nature, Vol. 332, p. 543 (1988) disclose a method for dissolving hair at pH 8 by the action of dithiothreitol, proteinase K, and 2% sodium dodecylsulfate in order to extract DNA from the digest by a complex chemical extraction method.

Also noted is the existence of certain patents, e.g., U.S. Pat. Nos. 3,986,926, 3,966,551, 3,939,040 and 3,623,950, which pertain to depilatory agents for the tanning of hides, and disclose the use of certain enzymes, including papain, in the dehairing process.

However, these and other prior art methods have proven disadvantageous for the reasons noted above and/or because they degrade the analyte probes (e.g., antibodies) of biological analytical methods, thereby preventing the use of such highly sensitive analytical techniques.

Thus, there exists a need for an analyte detection method that can rapidly and completely solubilize a certain analyte from keratinized structures of the body such as hair, fingernails, toenails and skin of a subject and which permits direct analysis of the identity of the analyte and the duration of use of the analyte in, or exposure to, a subject, without destroying the analyte of interest and/or an analyte probe of biological analytical methods.

SUMMARY OF THE INVENTION

It is an object of the invention to provide a drug and chemical detection method;

It is another object of the invention to provide a drug and chemical hair analysis method;

It is another object of the invention to provide a reliable method of solubilizing, and directly analyzing the identity of, analytes in head and body hair and other keratinized structures of the body, and, where applicable, of determining the duration and extent of exposure of the analyte in a subject;

It is yet another object of the invention to provide a hair analysis method that solubilizes an analyte from the inner core of hair without causing damage to the analyte;

It is yet another object of the invention to provide a reliable hair solubilization and direct analyte detection method that effectively permits the use of highly accurate biological analytical methods;

It is yet another object of the invention to provide a reliable hair analysis method that may be performed in a much less period of time than known hair analysis methods.

These and other objects are achieved by a novel keratinized structure analysis method which comprises preparing a mixture containing a low-redox potential compound such as dithiothritol (DTT) or dithioerythritol (DTE), an enzyme suitable for the dissolution of keratinized structures and a sample of a keratinized structure; permitting DTT or DTE to activate the keratinized structure and/or the enzyme; permitting the enzyme to at least substantially dissolve the sample of keratinized structure to form a keratin digest solution; and subjecting a portion of the keratin digest solution to analysis to detect the identity and amount of the analyte, if present, in the keratinized structure sample.

The preferred keratinized structure is hair. The enzyme may be selected from the group consisting of peptidase, endopeptidase, and protease and preferably is papain, chymopapain, or proteinase K. In order to accelerate the analytical process, cupric sulfate or sodium arsenite ($Na_2AsO_2$) may be added to the digest solution to deactivate interfering excess dithiothreitol or dithioerythritol in the mixture. Preferably, the analysis of the solubilized analyte is performed by a biological analytical method such as an immunoassay.

DETAILED DESCRIPTION OF THE INVENTION

In accordance with the present invention, a method is provided that permits the rapid and complete solubilization of a certain analyte from head or body hair or other keratinized structures of an individual who has previously been exposed to the analyte, e.g., has ingested the analyte, followed by the identification of the analyte by known analytical biological probes, such as the rapid and highly sensitive immunoassays. The solubilization of the analyte from the interior of hair is effectuated without damaging the analyte trapped within the organic matrix of the hair fiber which is to be analyzed, nor does it effect a subsequently-used probe (e.g., antibody) of a biological analytical method. The hair analysis method according to the invention also permits the detection of past use patterns in a subject over extended periods of time without performing repeated testing as is necessary in conventional analyte detection methods which measure the content of the analyte in samples of blood or urine.

More particularly, the invention comprises the rapid enzymatic digestion of the proteins making up samples of hair and other keratinized structures, followed by the effective deactivation of the enzyme and associated enzyme/substrate activator (DTT and DTE). The resultant solubilized analyte in the hair digest solution may then be analyzed by known biological analytical probes, preferably by highly sensitive protein-based analytical techniques such as immunoassay. It has been found that the amount of analyte entrapped in hair is directly proportional to the amount of analyte ingested.

In accordance with the invention, a sample of a keratinized structure, e.g., hair, is first collected from a subject suspected of having been exposed to, or having ingested, a particular analyte. Preferably, the hair sample is first washed by known methods to remove any analyte or other drug or chemical which may have been deposited on the surface of the hair by external contact rather than by actual consumption. The hair sample is then subjected to treatment with particular enzymes, together with a particular enzyme/substrate activator, so as to effectuate the complete or nearly complete dissolution of the organic matrix of the hair fiber, known as keratin. The subject analyte that has been "entrapped" within the organic matrix of the hair is then released into solution, or even if protein bound, the analyte is accessible to the antibody used in protein-based analytical methods. In order to fully and accurately carry out the method of the invention, a complete dissolution of the keratinized structure is desirable.

The enzymes preferred for the dissolution of the hair samples are those of the enzyme classes peptidase, endopeptidase and protease. Most active, and therefore preferred for use in the invention, are the enzymes papain, chymopapain and proteinase K.

A number of other proteases have been found to be effective in the method according to the invention at low pH values (e.g., pH 7–9), namely, protease Type IV (bacterial, from Streptomyces caespitosus), Type VIII (from *Bacillus subtilis*), Type XI (proteinase K, fungal, from *Tritirachium album*), Type XIV (pronase, from *Streptomyces griseus*), Type XVI (from *Bacillus subtilis*), Type XVIII (Newlase, from Rhizopus species), Type XIX (from *Aspergillus sojae*), Type XXI (from *Streptomyces griseus*), Type XXIV (bacterial), Type XXVII (Nagarase), Type III (Prolase), Type X (Thermophilic-bacterial Protease, thermolysin); and Type XXIII (from *Aspergillus Oryzae*).

As noted above, certain art-recognized procedures provide for the use of papain for use as a hair depilatory. These depilatory methods remove hair from hides and skin by softening it sufficiently so as to permit its ready removal by scraping or other mechanical means, and utilize inexpensive and less effective sulfhydryl enzyme and substrate activators such as thioglycolic acid or cysteine. Thus, these methods only partly degrade the hair and do not provide for the complete chemical dissolution of the hair. A mere softening of the hair would not be acceptable in a method providing for the analysis of hair for the detection of analyte, since only a complete, or nearly complete, dissolution of hair is acceptable in order to obtain a complete release of "entrapped" analyte. Moreover, the sulfhydryl enzyme activators used in these depilatory methods are also harmful to certain biological analyte probes such as antibodies.

In contrast to these depilatory methods, the method of the present invention utilizes dithiothreitol ("DTT", or 2,3-dihydroxybutane-1,4-dithiol) or its isomer dithioerythritol ("DTE", or 2,3 dihydroxybutane-1,4-dithiol) as the substrate and sulfhydryl-enzyme activating agent. Surprisingly, it has been found that DTT and DTE produce a highly active enzyme capable of dissolving hair within a relatively short period of time, e.g., about three hours, resulting in the release of the analyte into the hair digest solution. This high activity of the enzyme has been found to be due, at least in part, to the activation of the keratinized structure substrate itself by DTT and DTE, presumably by the action of DTT and DTE in opening up disulfide bonds in the keratinized structure, which facilitates enzymatic attack.

Once the protein of the keratinized structure has been completely or at least substantially dissolved, thereby releasing the analyte into the solution mixture, it has been found to be necessary to deactivate the enzyme and the enzyme/substrate activator(s) in order to subject the analyte to biological analytical probes such as antibodies, since the enzyme and enzyme/substrate activator(s), as noted above, can interfere with the structural integrity of protein substances involved in the analytical method.

The task of deactivating the sulfhydryl-dependent enzymes such as papain has proven difficult since after the hair digestion step, the enzymes are "buried" in a "sea" of sulfhydryl groups belonging to the released hair proteins and enzyme/substrate activating agents. Known sulfhydryl blocking agents are ineffective in deactivating the enzymes, since the known sulfhydryl blockers tend to bind to the degraded hair proteins and DTT or DTE and not necessarily to the enzyme sulfhydryl sites critical for blocking the activity of the enzymes. Thus, it is not possible to effectively utilize the protein-based analytical methods if the enzyme sulfydryl sites are still active.

Thus, it was surprisingly discovered that DTT and DTE act not only to activate enzymes and/or the keratinized structure substrate causing unexpectedly high hair digestion activity, but that they also spontaneously act to deactivate the enzyme by a direct or indirect (enzyme self-deactivation) mechanism after the enzyme effectuates the complete, or nearly complete, dissolution of the hair protein. Typically, the enzyme deactivation action of DTT or DTE occurs within about four to five hours after exposure to the enzyme, which is a sufficient amount of time for the enzyme to effectuate the dissolution of the hair sample. Once the enzyme has been deactivated, it has been found that the enzyme cannot be reactivated or regenerated by exposure to fresh DTT or DTE.

Deactivation of at least certain of the non-sulfhydryl dependent proteinases, e.g., proteinase K, by its inhibitor, phenylmethyl sulfonyl chloride, is generally not required since the enzyme has not been found to be active against the antibodies used in protein based immmunoassay techniques.

It has also been found that active DTT and DTE present in the hair digest solution constitute a hazard to the structure and activity of other proteins to which it is exposed, e.g., antibodies utilized in radioimmunoassay. Thus, it was a further surprising result that DTT or DTE in the reaction mixture will not only spontaneously act to deactivate the enzyme, but itself is spontaneously deactivated in the digest solution. Typically, the spontaneous deactivation of DTT or DTE will occur about 14 hours after its first exposure to the enzyme, depending on the various concentrations and amounts of the enzyme and DTT or DTE utilized, the pH, temperature, amount of hair sample, etc.

Thus, in accordance with the method of the invention, complete hair digestion can be carried out in a relatively short period of time, e.g., overnight, and the hair digest solution, which includes the released analyte of interest, can be directly subjected, effectively and accurately, to protein-based ligand assay analysis methods the next morning. Typically, the entire method, from the washing of hair samples to the identification of the analyte, should take no longer than about 16–20 hours. Little or no intervention by the individual performing the method is needed to release the analyte from the hair sample once the enzyme and DTT or DTE come into contact with the hair sample.

Alternatively, it has been discovered that the addition of cupric sulfate to the sulfhydryl group-rich hair digest solution acts to more rapidly deactivate the sulfhydryl groups of DTT or DTE. Thus, the addition of low amounts of the cupric sulfate to the hair digest mixture after digestion of the hair sample and the deactivation of the enzyme by DTT or DTE significantly accelerates the time in which the hair digest mixture can be subjected to the analysis method since it is not necessary to wait for the self-deactivation of DTT or DTE, which occurs approximately fourteen hours after its addition to solution. Typically, about 100 microliters of cupric sulfate (10 mg/ml) is added to 1 ml of hair digest mixture about 4 to 5 hours after contacting the enzyme and DTT or DTE with the hair sample so as to permit the enzyme sufficient time to dissolve the hair sample.

Similarly, sodium arsenite ($NaAsO_2$) may be utilized in the invention to remove residual DTT or DTE by formation of a precipitable compound. Typically, 100 microliters of a 100 mg/ml solution of sodium arsenite is added to 1 ml of hair digest solution to effectuate the deactivation of DTT and DTE.

Once the rapid and effective dissolution of hair for the purpose of releasing entrapped analytes is effectuated as described above, the analyte mixture may then be subjected to direct analysis by art recognized protein-based analytical methods such as radioimmunoassay ("RIA"). Such methods are preferred for use in the invention because RIA and related immuno- or ligand assays are currently the only known mass production procedures having the required sensitivity and convenience for measuring the low concentrations of analytes contained in hair samples. The use of these methods is preferred because only about 0.5 to 1.0 mg. of hair is necessary for analysis by RIA and other protein-based analytical methods. Indeed, for certain drugs-of-abuse, it has been found that analysis by the method according to the invention can be effectively performed on as little as one or two hairs about one inch in length.

Other analytical methods may be utilized in place of the protein-based analytical methods, including instrumental means such as chromatography, mass spectrometry, etc. Because these methods are not protein-based, the step of deactivation of the enzyme and DTT or DTE is not necessary when using non-protein-based analytical techniques. However, the speed and gentleness of the extraction method according to the invention and the ability to quantitate the extraction efficiency through the inclusion of a "spike", i.e., the inclusion of a known amount of analyte, makes the presently disclosed extraction method also the method of choice for instrumental analysis methods such as gas chromatography and mass spectrometry.

The method according to the invention has been found to be effective in detecting the use and prior use of drugs of abuse such as cocaine, morphine/heroin, marijuana, phenylcyclidine or "PCP", and methaqualone. Moreover, the method according to the invention has been found to be effective in determining prior usage of prescription drugs such as digoxin and amphetamines and toxic chemicals such as nicotine. It is contemplated that any organic analyte present in the bloodstream of an individual and transferred to the hair during its synthesis can be extracted and analyzed in accordance with the method of the invention.

In carrying out the method according to the invention, it is preferred that an aqueous solution of about 110 mg DTT or DTE/10 ml water be used, although concentrations of DTT or DTE of about 50–200 mg/10 ml water have been shown to be effective in the invention. It is preferred that the weight ratio of DTT or DTE to papain or chymopapain be about 110:2 [when enzyme purity is 16–40 BAEE units/mg protein], although efficacious results have been observed at weight ratios of DTT or DTE to papain or chymopapain ranging between about 110:1 to about 110:4. With respect to proteinase K and other proteases, it is preferred that the weight ratio of DTT or DTE to proteinase K (or other proteases) be about 1200:1 (when enzyme purity is 10–20 units per mg. protein), although weight ratios of 1200:0.5 to about 1200:2 will also be effective.

The concentration of hair protein is preferably kept constant at about 10 mg hair/cc of digest solution so as to prevent variable matrix effects in a subsequently utilized protein-based analytical method.

It is preferred that the enzymatic digestion of hair, according to the method of the invention, be conducted at low temperatures and near neutral pH. In this regard, it is preferred to perform the method, when papain or chymopapain is utilized as the enzyme, at a temperature of between about 20° C. and 40° C., and at a pH between about pH 8.8 and 10.5. Preferably, the pH is between about 8.8 and 9.5. In a most preferred embodiment, the temperature is about 37° C. and the pH about 9.1.

When proteinase K or other proteases are utilized as the enzyme, it is preferred to perform the method between about 20 and 40 degrees centigrade and at a pH between about 7 and 9. In the most preferred embodiment, the temperature is about 37 degrees centigrade and the pH about 7.0; under these conditions, the risk of damaging a particular analyte is at a minimum. Other enzymes which dissolve hair under neutral conditions include: Protease Type XIV (Pronase), Type IV, Type VIII, Type XXVII (Nagarase), Type XXVIII (Newlase), Type XXVIII, Type XVI, Type XXI and Type XXIII.

In another embodiment according to the invention, a filter is employed to remove certain ultrafine particulate substances present in the digest solution which may interfere with the biological screening method. It is most preferred that such a filter be employed when marijuana is the analyte of interest.

Certain ultrafine particulate substances (which may include melanin, digested hair proteins and lipid emulsions) are released into the digest solution when a hair sample is digested according to the invention. These substances may interfere with the immunoassay by creating interfering matrix effects. It is possible to remove such interfering substances by precipitation and solvent extraction procedures. However, these procedures are time consuming and are not conducive to a commercial drug assay method where time and expense need to be minimized. Similarly, high speed centrifugation is not cost effective. Thus it has been found to be desirable to employ a filtering technique to remove these interfering substances from the digest solution prior to subjecting the solution to analysis.

Many filtering techniques with the capability of filtering out small particles are not effective in filtering out the interfering particulate substances found in the digest solution. For example, certain filters will remove the analyte itself by absorption of the analyte on the filter.

It was thus unexpected that certain filters capable of removing proteins and peptides having molecular weights in the range of about 5,000 to 30,000 and greater are capable of removing the interfering substances without specifically affecting the concentration of analyte in the digest solution. These filters include the "Ultrafree®-MC" Filter Units of Millipore Corporation (Bedford, Mass.), catalog # UFC3 LGC (10,000 Nominal Molecular Weight Limit or NMWL)) and Millipore catalog # UFC3 LTK (new product # SK1 P343 JO) (30,000 NMWL). This type of filter is also known as a "membrane based centrifugal device". These filters are characterized by highly inert and low-binding, regenerated de-acetylated cellulose membranes. In general, filters of the centrifugal type having NMWL values of 30,000 or greater are preferred for use in the invention.

That these filters are effective in removing interfering substances and not the analyte, particularly marijuana, is surprising since one would have expected that a filter capable of removing high molecular weight keratin proteins (about 30,000 MW) from the digest solution would also remove a major portion of the marijuana analyte which is bound to keratin molecules under normal conditions. Without being bound by theory, it is believed that the failure of the analyte to be bound by the filters described herein at least partially is attributable to the displacement of marijuana from keratin by the ingredients of the hair digest mixture (most likely by DTT) and/or by the DTT induced structural changes of the keratin with accompanying loss of analyte (e.g., marijuana) binding capacity (i.e., shielding of lipophilic sites).

In practice, a sample of the digest solution (e.g., about 200 µl) is placed in the top of the filter at room temperature and the filters are centrifuged in microtubes to collect the filtered digest solution. The filtered digest solution containing the analyte of interest is then subjected to analysis as previously described herein.

While the problem described herein with interfering substances is particularly prevalent in marijuana assays, the filters described herein also have been found to be effective in improving the accuracy of the method according to the invention as it relates to other analytes, particularly methamphetamines.

In contrast to other available analyte detection methods such as urine and blood analysis, the method in accordance with the invention permits detection of exposure to an analyte over a period of time, and is therefore quite beneficial in detecting chronic drug use. Since hair is known to grow at a rate of about 0.3–0.4 mm/day or about 1.0–1.3 cm/month, it is possible to measure consumption or exposure as far back as the hair length permits by evaluating snippets of hair of various lengths, and the use of highly sensitive protein-based analytical methods permits analysis of small samples of analyte contained in the small snippets of hair.

Through sectional analysis, the method of the invention provides a relatively permanent record and evidence of a pattern of drug use, or the prior ingestion of other substances, for periods ranging from several days to months or even years after last use. The history of such exposure can be made as detailed as desired by analyzing suitably short sections of hair representing different periods of growth. In this way, prior usage over time, and the extent of such use, can be determined.

Although the use of head hair is preferred for use in the invention due to its length and accessability, it is possible to utilize any other body hair in the method of the invention. Thus, it is not practically possible to avoid testing by the method of the invention by shaving one's head.

However, treatments such as perming and dyeing may increase the rate of dissolution of hair subjected to the method according to the invention. In some cases, some analyte may be lost prior to performing the procedure due to such treatments. When the subject hair has been so altered, an increase in digestion rate is evident and an appropriate correction factor may be applied based upon known rates of normal hair dissolution.

Certain other cosmetic agents, such as certain relaxing agents, may cause hair to become resistant to digestion. Such resistance may be overcome by increasing the quantity of enzyme to be used. Preferably, proteinase K is utilized as the enzyme when such resistance to digestion is encountered.

Alternatively, when it is not possible to make use of body hair or in some instance when the use of hair is not desirable, the use of other keratinized tissue such as fingernails, toenails and skin may be used in the invention. In this regard, the effective ratio of DTT or DTE to enzyme needed to dissolve fingernails and toenails in order to release the analyte is about the same as for use with hair, as discussed above. Once the fingernail or toenail samples are dissolved in accordance with the method described herein, the released analyte may be analyzed by a desired analytical method.

In another aspect of the invention, it has been surprisingly discovered that melanin granules contained in hair can be dissolved by the combined action of the enzyme (preferably papain), DTT or DTE and ethylene diamine tetraacetic acid (EDTA), the latter at a concentration of about 5 mg EDTA/ml of digest solution. Since certain analytes or drugs of abuse such as PCP have been discovered to accumulate in these granules, dissolution of the granules, which are present in the digest solution of hair, can be effectuated and the analyte contained in the granule identified.

In accordance with this aspect of the invention, a hair digest solution is obtained as described above, and the melanin granules recovered from the hair digest solution, e.g., by centrifugation. The melanin granules are then contacted with EDTA, the enzyme and DTT or DTE to release the analyte from the melanin granules, and the analyte analyzed by the methods described above.

The benefits to be obtained from use of the method according to the invention are many. The method provides a prompt and accurate diagnosis of prior exposure to a particular analyte. The subject hair and keratinized structure analysis method can provide a record of consumption, or non-consumption, over very long periods of time. Guess work regarding the true significance of one blood or urine analysis will be eliminated. Hair collection is less intrusive and less physically repulsive than blood or urine collection, and samples cannot be altered or substituted, nor can detection be evaded by short term abstention or "flushing" (excessive fluid intake) prior to a scheduled testing, e.g., pre-employment test or annual physical examination. Samples may be stored indefinitely without refrigeration.

The methods according to the invention, useful for the dissolution of keratinized structures, e.g., hair, can also be used to ascertain the presence and structure of naturally occurring components of hair such as DNA.

The following examples illustrate certain aspects of the invention but they do not limit the invention as set forth in the specification and claims.

EXAMPLE 1

Extraction of Cocaine from Hair Sample 10 mg of hair was removed from a subject suspected of being a cocaine addict and washed by shaking in water at 37° C. for 30 minutes. To 10 ml. of distilled water, 110 mg. of dithiothreitol (2,3-dihydroxybutane-1,4-dithiol, Cleland's reagent, obtained from Sigma Chemical Co., St. Louis, Mo.), was added. The pH of the solution was adjusted to pH 9.1 with 15% potassium hydroxide added dropwise with stirring of the DTT solution. Stirring was continued while adding 80 microliters of Type III papain solution (papainase EC 3.4.22.2) (obtained from Sigma Chemical Co., 16–40 BAEE units activity per mg. protein). The enzyme solution was at a concentration of 30 mg of enzyme protein/ml of water, where 1 mg of enzyme protein has an activity of 16–40 BAEE units [one BAEE unit will hydrolyze 1.0 micromole of sodium benzoyl-L-arginine ethylester at pH 6.2 at 25° C.].

To 1 ml of this solution was added the 10 mg hair sample in a 13×75 mm polycarbonate test tube. The solution was incubated in a 37° C. water bath with shaking for 2 hours, and the solution was allowed to stand overnight at 37° C. without shaking. The solution containing the dissolved hair sample was centrifuged at 2,000 rpm [Damon IEC model CRU 5,000 centrifuge] to remove the melanin granules. To 1 cc of the hair digest solution was added 200 microliters of a 1 molar phosphate buffer, pH 5.5.

100 microliters of this solution was assayed by RIA for the presence of cocaine [benzoylecgonine equivalent, or "BEE"]. RIA analysis revealed 83.6 nanograms BEE/10 mg of hair.

EXAMPLE 2

Addition of Dithioerythritol

The hair sample of Example 1 was analyzed using the digestion and assay procedure set forth in Example 1, except for the replacement of dithiothreitol (DTT) by dithioerythritol (DTE). The sample was assayed by RIA, which revealed 82 nanograms cocaine (BEE) per 10 mg of hair.

EXAMPLE 3

Addition of Cupric Sulfate

After digesting the hair sample in the water bath for four hours, 100 microliters of a 10 mg/ml cupric sulfate solution was added to 1 ml of the hair digest solution prepared as set forth in Example 1. The solution was shaken at 37° C. for about 30 minutes prior to the addition of phosphate buffer and assay by RIA. One hundred microliters of the hair digest solution was subjected to RIA analysis, which revealed 85.0 nanograms of cocaine (BEE)/10 mg of hair.

EXAMPLE 4

Addition of Sodium Arsenite

After digesting the hair sample in the water bath for four hours, 100 microliters of a 100 mg/ml sodium arsenite solution was added to 1.0 ml of the hair digest solution prepared as set forth in Example 1. The solution was shaken at 37° C. for 30 minutes. 200 microliters of 1M, pH 6.5, phosphate buffer was added prior to assay by RIA. One hundred microliters of the hair digest solution was subjected to RIA analysis, which revealed 82 nanograms of cocaine (BEE) per 10 mg of hair.

EXAMPLE 5

Substrate Activation by Dithiothreitol (DTT)

10 mg of hair were exposed to 11 mg of DTT at pH 9.1 for a period of 20 hours. The DTT solution was removed and replaced with DTT and papain as in EXAMPLE 1. The hair specimen dissolved within 10 minutes as compared to within one hour for a control specimen not pretreated with DTT and digested as in EXAMPLE 1, thereby demonstrating that DTT activated not only the sulfhydryl-dependent enzyme, papain, but the enzyme substrate, hair, as well.

EXAMPLE 6

Digestion and Analysis of Hair Using Proteinase-K 10 mg of hair was removed from a subject suspected of being a cocaine user and washed by shaking in water at 37 degrees centigrade for 60 minutes. To 10 ml of 0.05 M TRIS buffer, pH 7.0, 60 mg of dithiothreitol (DTT) and 20 mg sodium dodecyl sulfate (lauryl sulfate) was added. The pH of the solution was checked to ensure the solution was buffered at a pH 7.0. To this solution was added 0.5 mg proteinase K [Protease Type XI, from Tritirachium album, obtained from Sigma Chemical Co.; 1 mg of enzyme protein has an activity of 10–20 units; one unit will hydrolyze casein to produce color equivalent to 1.0 umole (181 μg) of tyrosine per minute at pH 7.5 at 37 degrees centigrade (color by Folin-Ciocalteu reagent)].

To 1 ml of this solution was added the 10 mg hair sample in a 13×75 mm polycarbonate test tube. The solution was incubated in a 37° C. water bath with shaking for 1 hour and allowed to stand overnight at 37° C. without shaking. The solution containing the dissolved hair sample was centrifuged at 2,000 RPM to remove the melanin granules. To 1 cc of the hair digest solution was added 100 microliters of Cupric Sulfate (10 mg/ml), and this solution was shaken at 37° C. for 30 minutes. 200 ul of 1 M phosphate buffer, pH 7.0, was then added.

100 microliters of this solution was assayed by RIA for the presence of cocaine (benzoylecgonine equivalents, or BEE). RIA analysis revealed 31.2 nanograms BEE/10 mg of hair.

EXAMPLE 7

Role of Sulfhydryl Compounds in the Activation of Hair for Proteinase K Digestion 10 mg of hair was incubated in a solution identical to that described in EXAMPLE 6 except that DTT was omitted.

No digestion of hair occurred during 24 hours of enzyme exposure, thereby demonstrating the need for the activation of the hair sample by the substrate activator, DTT.

EXAMPLE 8

Dissolution of Fingernails

A 10 mg. sample of fingernail clippings was obtained from a subject, and subjected to a detergent wash. 220 mg of DTT was added to 10 ml of water in a test tube and the pH adjusted to pH 9.1 as in Example 1. A papain suspension, 160 microliters, was then added. 1.0 ml of this solution was then added in a test tube to 10 mg of fingernail clippings and shaken at 37° C. for a period of 24 hours until dissolution occurred. The digest solution was then analyzed by RIA as previously described.

EXAMPLE 9

Performance of Sectional Analysis

A hair sample, about 6 cm in length, was obtained from an individual suspected of being a heroin addict. The samples were carefully sectioned into three 2 cm sections, with corresponding sections added to three separate test tubes and washed. The hair samples were subjected to the process described in Example 1, except that chymopapain (EC 3.4.22.6) was used in place of papain as the enzyme. The samples were agitated overnight as previously described.

RIA analysis revealed morphine content in the three sections of 13.5, 5.7 and 0 nanograms/10 mg hair.

EXAMPLE 10

Dissolution of Digestion-Resistant Hair

Ten milligrams of hair which had been treated with relaxer was incubated overnight in the solution digest described in Example 6. The hair sample did not dissolve in the usual 20-hour period. A greater and additional amount of proteinase K, i.e., 1 mg, was then added to the partially digested sample. The sample then dissolved within the next 24 hours. The digest was centrifuged and 100 ul $CuSO_4$ solution (10 mg/ml) was added to 1 ml of the supernatant which was then shaken at 37 degrees centigrade for 30 minutes. 200 ul of 1 M phosphate buffer pH 7 was added. Due to the high amount of proteinase K in the resulting digest, 20 ul of the proteinase inhibitor phenylmethyl sulfonyl chloride in ethanol was added to the digest prior to assay by RIA.

RIA analysis revealed 7.4 ng cocaine (BE)/10 mg hair.

EXAMPLE 11

Digestion of Hair using Papain and Filtration of Digest Solution to Remove Interference in Marijuana RIA Assay 10 mg of hair from each of 6 known normal subjects (not marijuana users) and 10 mg of hair from 1 known marijuana user were placed in separate 13×75 mm polycarbonate tubes. 1.0 ml of a solution containing papain and 110 mg dithiothreitol at pH 9.1 was added to each tube. The mixtures were shaken 16 hours at 37° C. After 16 hours, the samples were centrifuged at 3,000 RPM for 20 minutes followed by the addition of 90 µl of $CuS_4O.5H_2O$ (10 gm/liter) to the supernatant of each sample. The mixtures were shaken at 37° C. for 30 minutes. 180 ul of 1 M phosphate buffer of pH 6.5 was added. 200 µl of each sample were placed in a Millipore Corporation, Bedford, Mass., UFC3 LGC 10,000 MW cut-off filtration device and the filtration devices were centrifuged at 3500 RPM for 1 hour. 150 µl of the filtrate of each sample was then assayed for marijuana by RIA. Results were as follows:

| | |
|---|---|
| Sample 1 (known negative) | 4754 cpm |
| Sample 2 (known negative) | 4561 cpm |
| Sample 3 (known negative) | 5180 cpm |
| Sample 4 (known negative) | 4771 cpm |
| Sample 5 (known negative) | 4803 cpm |
| Sample 6 (known negative) | 4538 cpm |
| Sample 7 (known positive) | 1377 cpm |

Sample 7 demonstrated a $B/B_o$ (value of sample containing marijuana/value of sample not containing marijuana) of 29% as compared to known negative samples (100%), indicating a positive result for the presence of marijuana in Sample 7.

EXAMPLE 12

Digestion of Hair using Proteinase K and Filtration of Digest Solution to Remove Interference in Marijuana Assay 10 mg of hair from each of 3 known normal subjects (not marijuana users) and 10 mg of hair from 1 known marijuana user were placed in separate 13×75 mm polycarbonate tubes. 1.0 ml of the following solution was added to the hair in each of the tubes: 0.5M Tris buffer (pH 6.5 at room temperature) containing in one ml 2 U Proteinase K, 2 mg cholic acid (sodium salt), and 60 mg dithiothreitol. The mixtures were shaken 16 hours at 37° C. After 16 hours, the samples were centrifuged at 3,000 RPM for 20 minutes. To 0.9 ml of supernatant removed after centrifugation was added 10 µl of phenylmethylsulfonyl fluoride (6% in ethanol). This was mixed, followed by the addition of 90 µl $CuSO_4.5H2O$ (10 gm/liter). The mixtures were shaken at 37° C. for 30 minutes. 200 µl of each sample was placed in a Millipore Corporation UFC3 LGC, 10,000 MW cut-off filtration device and the filtration devices were centrifuged at 3500 RPM for 1 hour. 100 µ of the filtrate of each sample was then assayed for marijuana by RIA. Results were as follows:

| | |
|---|---|
| Sample 1 (known Negative) | 6657 cpm |
| Sample 2 (known Negative) | 6661 cpm |
| Sample 3 (known Negative) | 6227 cpm |
| Sample 4 (known Positive) | 3336 cpm |

Sample 4 demonstrated a $B/B_o$ of 51% as compared to negative samples (100%), a positive result for the presence of marijuana in Sample 4.

While there have been described what are presently believed to be preferred embodiments of the invention, it will be apparent to one skilled in the art that numerous changes can be made in the ingredients, conditions and proportions set forth in the foregoing embodiments without departing from the invention as described herein and as defined in the appended claims.

What is claimed is:

1. A method for the detection of marijuana intake by an individual which comprises:
   (a) preparing a mixture comprising a sample of keratinized structure from the individual, an agent selected from the group consisting of dithiothreitol and dithioerythritol and a sulfhydryl-dependent protease suitable for the digestion of keratin; the amounts of the agent and the protease being sufficient to effectuate the digestion of the sample;
   (b) permitting the digestion of the sample to form a keratin digest solution, said solution comprising an analyte characteristic of marijuana intake if present in the sample and an interfering substance that may interfere with a marijuana immunoassay;
   (c) permitting the passage of a sufficient period of time for the agent and the protease to become deactivated such that the agent and the protease will not interfere with the accuracy of an immunoassay method performed on the digest solution;
   (d) filtering the digest solution through a filter to remove the interfering substance, said filter being characterized by a highly inert and low-binding de-acetylated cellulose membrane capable of removing proteins and peptides having molecular weights in the range of about 5,000 to about 30,000; and
   (e) after the agent and protease have deactivated, and the interfering substance has been removed, subjecting a portion of the filtered digest solution to analysis by immunoassay to detect the analyte if present.

2. The method according to claim 1 further comprising the step of adding cupric sulfate to the solution after the keratinized structure has been digested and before the keratin digest solution is subjected to analysis in an amount sufficient to deactivate the agent such that the amount of time necessary for the deactivation of the agent is decreased.

3. The method according to claim 1 wherein the keratinized structure sample is digested at a temperature between about 20° C. and 40° C., and at a pH between about 8.8 and 10.5.

4. The method according to claim 1 wherein the keratinized structure sample is digested at a pH of about 9.1 at a temperature of about 37° C.

5. The method according to claim 1 wherein the keratinized structure sample is digested at a pH between about 8.8 and 9.5.

6. A method for the detection of marijuana intake by an individual which comprises:
   (a) preparing a mixture comprising an agent selected from the group consisting of dithiothreitol and dithioerythritol, proteinase K and a sample of keratinized structure; the amounts of the proteinase K and the agent being sufficient to effectuate the digestion of the sample;
   (b) permitting the digestion of the sample of keratinized structure to form a keratin digest solution, said solution comprising an analyte characteristic of marijuana intake if present in the sample and an interfering substance that may interfere with a marijuana immunoassay;
   (c) permitting the passage of a sufficient period of time for the agent to become deactivated such that said agent will not interfere with the accuracy of an immunoassay method performed on the digest solution;
   (d) filtering the keratin digest solution through a filter to remove the interfering substance from the digest solution, said filter being characterized by a highly inert and low-binding de-acetylated cellulose membrane capable of removing proteins and peptides having molecular weights in the range of about 5,000 to about 30,000; and
   (e) after the agent has deactivated, and the interfering substance has been substantially removed, subjecting a portion of the keratin digest solution to analysis by immunoassay to detect the analyte if present.

7. The method according to claim 6 wherein the keratinized structure sample is digested at a pH between about 7 and 9 at a temperature between about 20 and 40 degrees centigrade.

8. The method according to claim 6 further comprising the step of adding a substance selected from the group consisting of arsenite and cupric sulfate to the solution after the keratinized structure has been digested and before the keratin digest solution is subjected to direct analysis in an amount sufficient to deactivate the agent such that the time necessary for the deactivation of the agent is decreased.

9. A method for the detection of marijuana intake by an individual which comprises:
   (a) chemically treating a sample of hair from the individual in a manner that releases into solution an analyte characteristic of marijuana intake if present in the hair sample and an interfering substance that may interfere with a marijuana immunoassay;
   (b) filtering the digest solution through a filter to remove the interfering substance, said filter being characterized by a highly inert and low-binding de-acetylated cellulose membrane capable of removing proteins and peptides having molecular weights in the range of about 5,000 to about 30,000; and
   (c) after the interfering substance has been removed from the digest solution, subjecting a portion of the digest solution to analysis by immunoassay to detect the analyte if present.

10. A method for the detection of marijuana intake by an individual which comprises:
    (a) chemically treating a sample of hair from the individual in a manner that releases into solution an analyte characteristic of marijuana intake if present in the hair sample and an interfering substance that may interfere with a marijuana immunoassay;
    (b) filtering the digest solution through a membrane based centrifugal filter to remove the interfering substance, said filter being characterized by a highly inert and low-binding de-acetylated cellulose membrane capable of removing proteins and peptides having molecular weights in the range of about 5,000 to about 30,000; and
    (c) after the interfering substance has been removed from the digest solution, subjecting a portion of the digest solution to analysis by immunoassay to detect the analyte if present.

11. A method for the detection of marijuana intake by an individual which comprises:
    (a) chemically treating a sample of hair from the individual in a manner that releases into solution an analyte characteristic of marijuana intake if present in the hair sample and an interfering substance that may interfere with a marijuana immunoassay;

(b) filtering the digest solution through a filter to remove the interfering substance, said filter being characterized by a highly inert and low-binding de-acetylated cellulose membrane capable of removing proteins and peptides having molecular weights in the range of about 30,000 and greater; and (c) after the interfering substance has been removed from the digest solution, subjecting a portion of the digest solution to analysis by immunoassay to detect the analyte if present.

\* \* \* \* \*